(12) United States Patent
Tominaga et al.

(10) Patent No.: US 8,168,198 B2
(45) Date of Patent: May 1, 2012

(54) THERAPEUTIC AGENT FOR POLYCYSTIC OVARY SYNDROME (PCOS)

(76) Inventors: Kunihiko Tominaga, Fukushima-ken (JP); Hideo Anzai, Ridgewood, NJ (US); Cun Zhuang, Fort Lee, NJ (US)

( * ) Notice: Subject to any disclaimer, the term of this patent is extended or adjusted under 35 U.S.C. 154(b) by 73 days.

(21) Appl. No.: 12/535,308

(22) Filed: Aug. 4, 2009

(65) Prior Publication Data

US 2009/0291100 A1    Nov. 26, 2009

Related U.S. Application Data

(63) Continuation of application No. 11/573,726, filed as application No. PCT/JP2005/001697 on Feb. 4, 2005, now abandoned.

(30) Foreign Application Priority Data

Aug. 27, 2003    (JP) .................................. 2003-303462

(51) Int. Cl.
*A61K 36/06*    (2006.01)
(52) U.S. Cl. .................................... 424/195.15; 514/899
(58) Field of Classification Search .................. None
See application file for complete search history.

(56) References Cited

U.S. PATENT DOCUMENTS

| | | |
|---|---|---|
| 7,214,778 B2 | 5/2007 | Zhuang et al. |
| 2005/0014683 A1 | 1/2005 | Zhuang et al. |

FOREIGN PATENT DOCUMENTS

| | | |
|---|---|---|
| JP | 2004-300104 | 10/2004 |
| KR | 2002081825 A | 10/2002 |
| WO | 2006-082649 A1 | 10/2006 |

OTHER PUBLICATIONS

Ushiroyama, T. Reproductive Medicine and Biology (2003); 2: 45-61. Endocrinological actions of Unkei-to, a herbal medicine, and its clinical usefulness in anovulatory and/or infertile women.*

Yaichiro Yukimura et al; Treatment for Sterility using Kampo, Japanese Traditional Medicine, in Patients with Polycystic Ovaries and Pituitary Microadenomas; 1983, pp. 228-232, vol. 31; Shinshu Medical Journal, Japan.

Kubo, Keiko et al, Mushroom Biology & Mushroom Products (1996), pp. 215-221. Anti-diabetic mechanism of maitake (*Grifola frondosa*).

Kubo, Keiko et al, Anti-diabetic activity present in the fruit body of *Grifola frondosa* (maitake), Biol. Pharm. Bull. 17(8): 1106-1100 (1994).

European Patent Office, Search Report with corrected/revised 210 and 237 forms in Application No. PCT/JP2005/001697 dated Mar. 15, 2005; 12 pages.

* cited by examiner

*Primary Examiner* — Michele Flood
(74) *Attorney, Agent, or Firm* — Wood, Herron & Evans, LLP

(57) ABSTRACT

A therapeutic agent for treating polycystic ovary syndrome (PCOS), which exhibits few, if any, side effects, is effective at inducing ovulation, and is safely available for not only females who desire to bear children, but also for unmarried or young females. A therapeutic agent for polycystic ovary syndrome (PCOS) in which an extract of mushrooms is contained as the active ingredient thereof is used.

5 Claims, 3 Drawing Sheets

THERAPEUTIC AGENT FOR POLYCYSTIC OVARY SYNDROME (PCOS)

CROSS-REFERENCE TO RELATED APPLICATIONS

This application is a continuation of pending U.S. patent application Ser. No. 11/573,726 entitled "THERAPEUTIC AGENT FOR POLYCYSTIC OVARY SYNDROME (PCOS)", filed Feb. 15, 2007, which is a U.S. National Phase of PCT/JP2005/001697, filed Feb. 4, 2005, the disclosures of which are hereby incorporated by reference herein. This application is also related to Japanese application No. 2003-303462, filed Aug. 27, 2003.

TECHNICAL FIELD

The present invention relates to an effective and safe therapeutic agent for treating polycystic ovary syndrome (PCOS), which is a cause of female sterility, menstrual disorder, acne, excess hair growth, obesity, or the like.

BACKGROUND ART

Recent studies have reported that 6% of women of reproductive age suffer from polycystic ovary syndrome (PCOS). Moreover, it is predicted that the actual number of patients with potential polycystic ovary syndrome (PCOS) is much higher than this. Polycystic ovary syndrome (PCOS) means the state in which a follicle is not sufficiently matured for ovulation to occur and an ovary is filled with numerous small immature ova. Thus, ovulation disorder is caused.

The reason for this is believed to be because the balance between FSH (follicle-stimulating hormone) and LH (luteinizing hormone) in gonadotropic hormones (gonadotropins), which are secreted from the pituitary gland and required to induce ovulation, is not properly maintained. However, there are still many factors that have not yet been clarified.

Polycystic ovary syndrome (PCOS) results in irregular menstruation, loss of menstrual periods, menorrhagia, an increase of male hormones (testosterone), obesity, sterility, and other problems. As conventional methods for treating polycystic ovary syndrome (PCOS), the following medications and surgical procedures are known.

(I) Treatment Using an Ovulation-Inducing Agent (Clomiphene, Clomid)

Although this is a treatment in which clomiphene acts on the hypothalamic area to induce ovulation, there are cases in which ovulation does not always occur.

(II) Treatment Using Clomiphene Concomitantly with Another Agent

This is a treatment in which clomiphene is used concomitantly with other agents such as a steroid hormone and/or HMG (human menopausal gonadotropins), when no effects are exhibited by administering clomiphene alone.

(III) Treatment Using Gonadotropin (Method in which HMG or FSH is Administered)

This is a treatment method in which a gonadotropic hormone (gonadotropin) is injected into a patient so as to induce ovulation by stimulating the ovary. Although this treatment exhibits relatively high efficacy and a good pregnancy rate, there are some side effects such as multiple pregnancy and ovarian hyperstimulation syndrome (OHSS).

(IV) Administration of Shakuyaku-Kanzo-to

This is a treatment in which Shakuyaku-kanzo-to, a Chinese herbal medicine, is administered with few, if any, side effects, but its effect is not satisfactory.

(V) Laparoscopic Treatment

This is a treatment in which a laparoscope is used to form a small hole by radiating laser beams on the surface of the ovary. The problem is that this treatment is not a definitive treatment and is invasive to the living body.

(VI) Administration of Oral Contraceptive Agents

A treatment using hormonal agents such as oral contraceptive agents or the like to cause periodic menstruation is conducted for unmarried or young females suffering from polycystic ovary syndrome (PCOS) and who have no desire to bear children (pregnancy).

DISCLOSURE OF THE INVENTION

Problems to be Solved by the Invention

For sterile females suffering from polycystic ovary syndrome (PCOS) and who desire to bear children, the treatments aiming to induce ovulation as described above are mainly employed. Among them, the treatments using the ovulation-inducing agents as described in any of (I) to (III) are considered effective, but they still have a possibility of causing serious side effects such as multiple pregnancy or ovarian hyperstimulation syndrome (OHSS), and thus cause difficult problems.

Moreover, there is another problem in the treatment for unmarried females or young females. Many of these patients are reluctant to consult obstetricians or gynecologists and are often left without receiving proper medical attention. Such patients will be in danger where symptoms such as hypertrophy of the ovary membrane or the like will further progress and, thus, the treatment thereof becomes even more difficult.

Also, even when unmarried or young female patients consult obstetricians or gynecologists, both the doctors and the patients tend to avoid, as much as possible, treatment using strong agents such as an ovulation-inducing agent or gonadotropin, as described in (I) to (III) above. Also, the administration of the oral contraceptive agents described in (IV) is not favored by the patients. Accordingly, the patients are often diagnosed as having "irregular menstruation" or the like to receive only temporary relief against the symptoms.

Thus, conventional methods for treating polycystic ovary syndrome (PCOS) have the problems as described above and cannot satisfy the efficacy and the preventability of side effects. Moreover, recent studies have reported that the patients affected with polycystic ovary syndrome (PCOS) have a seven-fold risk of developing diabetes complications compared with unaffected individuals. As is well known, diabetes is a serious disease which could result in myocardial infarction, cerebral stroke, renal insufficiency, loss of eyesight caused by retinopathy, or the like. Accordingly, it is necessary that patients with polycystic ovary syndrome (PCOS) be treated at a stage before diabetes complications develop.

The present invention has been achieved in consideration of the above-mentioned situation, and has as an object thereof to provide a therapeutic agent for polycystic ovary syndrome (PCOS) which exhibits few, if any, side effects, is effective at inducing ovulation, and is safely available to not only females who desire to bear children, but also for unmarried or young females.

Means for Solving the Problems

As a result of extensive investigation on a safe and effective therapeutic agent for treating polycystic ovary syndrome (PCOS) to solve the above-mentioned problems, the inventors of the present invention have found that an extract of mushrooms exhibits activities effective against polycystic ovary syndrome (PCOS), and thereby completing the present invention.

That is, the present invention relates to a therapeutic agent for treating polycystic ovary syndrome (PCOS) containing an extract of mushrooms as an active ingredient thereof.

It is preferable that the mushrooms be at least one selected from the group consisting of *Grifola frondosa, Polyporus umbellatus, Meripilus giganteus, Grifola albicans, Lentinus edodes, Agaricus blazei Murill, Agaricus bispirus, Ganoderma applanatum, Fomitopsis pinicola, Coriolus versicolor, Ganoderma lucidum, Pleurotus ostreatus, Pleurotus eryngii, Hericium erinaceus, Cordyceps sinensis, Cordyceps sobolifera, Auricularia auricula, Tremella fuciformis,* and *Phellinus linteus*.

Moreover, it is more preferable that the mushrooms be at least one selected from the group consisting of *Grifola frondosa, Lentinus edodes, Agaricus blazei Murill, Ganoderma lucidum,* and *Pleurotus ostreatus,* among which *Grifola frondosa* is most preferable.

Also, it is preferable that the above-mentioned extract of mushrooms be prepared by a process including: (1) a step of treating a raw material of mushrooms (the fruiting body and/or mycelium are collectively called "raw material of the mushrooms") with ethanol having a concentration of 90% or more, and thereby removing ethanol-soluble components, (2) a step of extracting the residue with hot-water thereafter, adding the ethanol to the obtained hot-water-extracted liquid until a final ethanol concentration becomes 50 to 75% by value, removing produced insoluble components, and thereby obtaining a supernatant, and (3) a step of collecting a fraction having a molecular weight of 14,000 Dalton or more from the obtained supernatant.

Effects of the Invention

The therapeutic agent for polycystic ovary syndrome (PCOS) obtained under the present invention contains the extract of mushrooms as the active ingredient thereof, which is safe, exhibits few, if any, side effects, demonstrates excellent effects of inducing ovulation, and is safely available for not only females who desire to bear children, but also for unmarried or young females.

BEST MODE FOR CARRYING OUT THE INVENTION

Figure 1:
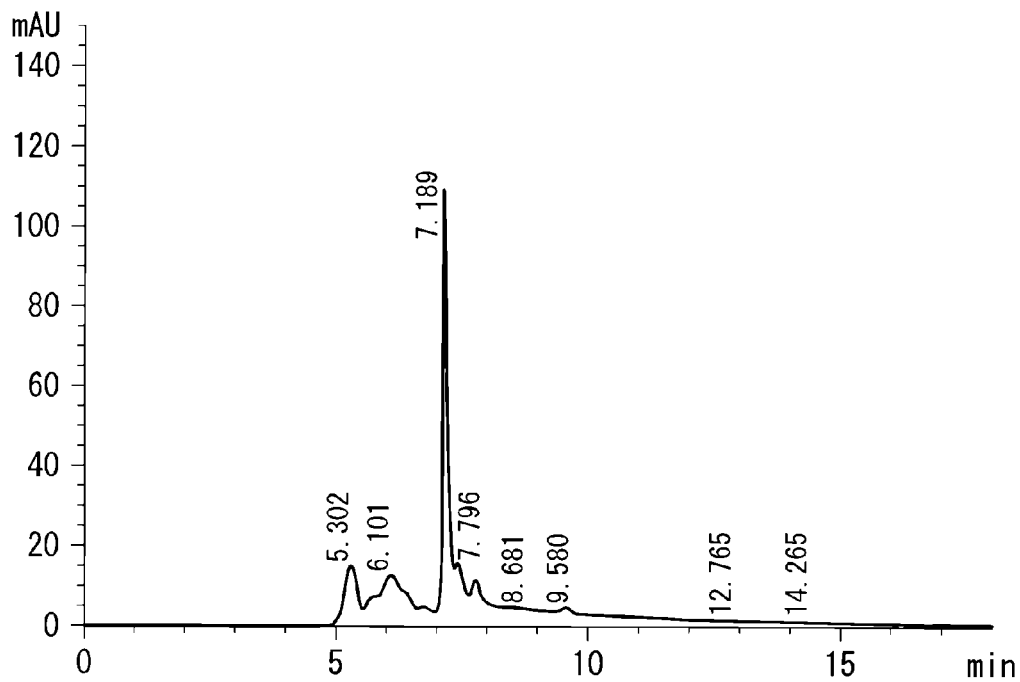
FIG. 1 is a chart drawing indicating a result of an analysis using high-performance liquid chromatography (HPLC) on an extract of *Grifola frondosa* obtained in Preparation Example 1. (Analysis Example)

The therapeutic agent for polycystic ovary syndrome (PCOS) obtained under the present invention contains an extract of mushrooms as the active ingredient thereof. This extract of mushrooms can be used in a therapeutic treatment for polycystic ovary syndrome (PCOS). Also, this extract of mushrooms can be used for preparing therapeutic agents for treating polycystic ovary syndrome (PCOS).

It is preferable that the mushrooms be at least one selected from the group consisting of *Grifola frondosa, Polyporus umbellatus, Meripilus giganteus, Grifola albicans, Lentinus edodes, Agaricus blazei Murill, Agaricus bispirus, Ganoderma applanatum, Fomitopsis pinicola, Coriolus versicolor, Ganoderma lucidum, Pleurotus ostreatus, Pleurotus eryngii, Hericium erinaceus, Cordyceps sinensis, Cordyceps sobolifera, Auricularia auricula, Tremella fuciformis,* and *Phellinus linteus,* in view of being used as food or medicine and having been highly prized and deemed to provide health benefits since ancient times.

Among them, it is more preferable that the mushrooms be at least one selected from the group consisting of *Grifola frondosa, Lentinus edodes, Agaricus blazei Murill, Ganoderma lucidum,* and *Pleurotus ostreatus. Grifola frondosa* is most preferable.

These mushrooms contain a glycoprotein, which is a saccharide-bound protein (conjugated protein), and the extract of the mushrooms according to the present invention is deemed to contain this glycoprotein as a main component thereof The glycoprotein, which is the main component of the extract of mushrooms under the present invention, is brown and exhibits water-solubility and thermal stability, and it is preferable that the mass ratio of a protein portion to a saccharide portion be in a range from 75:25 to 90:10, and the distribution of molecular weight be in a range from 18,000 to 22,000 Dalton, and be positive in a biuret reaction and Fehling's reaction. The term "protein portion" used herein means a portion composed of only a polypeptide chain in the glycoprotein that is a conjugated protein.

It is preferable that the distribution of the molecular weight of glycoprotein be in a range from 18,000 to 22,000 Dalton, and it is more preferable that the average molecular weight be 20,000. Thermal stability means that bioactivity is not lost when left to stand at a temperature from 80 to 130° C. for 1 to 5 hours.

Also, it is preferable that the extract of mushrooms under the present invention be prepared by a process including: (1) a step of treating a raw material of the mushrooms (the fruiting body and/or mycelium) with ethanol having a concentration of 90% or more, and thereby removing ethanol-soluble components, (2) a step of extracting the residue with hot-water thereafter, adding the ethanol to the obtained hot-water-extracted liquid until a final ethanol concentration becomes 50 to 75% by value, removing produced insoluble components, and thereby obtaining a supernatant, and (3) a step of collecting a fraction having a molecular weight of 14,000 Dalton or more from the obtained supernatant.

The method for producing the extract of mushrooms under the present invention includes the above-mentioned steps (1) to (3). First of all, the raw material of mushrooms used in the present invention is treated with ethanol having a concentration of 90% or more to remove ethanol-soluble components, as the first step (1).

As the raw material of mushrooms used in the present invention, fresh or dried mushrooms described above can be used without any particular limitations. Among them, dried powder is preferably used to conduct effective treatment. The ethanol having a concentration of 90% or more may be water containing 90% or more of ethanol (an aqueous ethanol). Among them, water containing 95% or more of ethanol is preferable, and 100% ethanol is most preferable, in view of effectively removing the ethanol-soluble components eluted from the raw material of mushrooms.

In the treatment of step (1), an ethanol or aqueous ethanol is added to the raw material of mushrooms and then stirred. At this time, it is preferable that the content of the raw material of mushrooms be 10 to 25% by mass, and more preferably 10 to 12.5% by mass. Also, although the temperature for the extraction is generally set from 20 to 70° C., it may be room temperature. Although the treatment time is dependent on the state of the raw material of mushrooms used, the treatment temperature, or the like, it is preferable to be 1 to 10 hours, and more preferably 2 to 3 hours.

By conducting this treatment, components soluble in ethanol are dissolved into the ethanol or aqueous ethanol from the raw material of mushrooms. Since the ethanol-soluble components are not required, the components are removed by filtration or centrifugation. Among them, centrifugation is preferable in the case that a large amount of the extract is required for experiment or commercialization.

Next, in step (2), a residue remaining after the ethanol-extraction in which the ethanol-soluble components are removed is subject to a hot-water extraction, the ethanol is added to the obtained hot-water-extracted liquid until the final ethanol concentration becomes 50 to 75% by value, and produced insoluble components are then removed to obtain a supernatant.

In the hot-water extraction, water is added to the residue remaining after the ethanol-extraction in step (1) and then heated. At this time, it is preferable that the content of the residue remaining after the ethanol-extraction be 10 to 25% by mass, and more preferably 10 to 12.5% by mass. Also, it is preferable that the temperature for extraction be 80 to 130° C., and more preferably 100 to 120° C. Also, it is preferable that the extraction time be 1 to 5 hour(s), and more preferably 2 to 3 hours.

Next, the residue of extraction is filtered off, and the ethanol is added to the hot-water-extracted liquid, which is a filtrate obtained by the filtration, until the final ethanol concentration becomes 50 to 75% by value. It is preferable that the hot-water-extracted liquid be concentrated to ⅓ to ½ of the original volume before adding the ethanol.

After adding the ethanol, it is preferable that the production of insoluble components such as precipitates or floating matter be promoted by allowing it to stand at a low temperature, preferably 0° C. to room temperature, and more preferably 4 to 10° C., for 5 to 24 hours, and more preferably 8 to 12 hours. After that, the produced insoluble components are removed by centrifugation or filtration to obtain a supernatant such as a filtrate or the like. By removing the insoluble components produced by adding the ethanol, substances having an immunosuppressive effect or the like can be substantially removed from the final product.

Next, in step (3), a fraction having a molecular weight of 14,000 Dalton or more is collected from the obtained supernatant. It is preferable that the collection of the fraction having a molecular weight of 14,000 Dalton or more be carried out by conducting dialysis or ultrafiltration. There are no particular limitations imposed on a dialysis filter used for this dialysis or ultrafiltration, provided that the filter has an ability to collect any fraction with a molecular weight of more than 14,000 Dalton, and generally-used filters such as a cellophane filter or collodion filter can be used.

After that, the obtained fraction having a molecular weight of 14,000 or more may be further purified for the purpose of increasing the purity thereof. As such a purifying method, a method usually used for purifying glycoprotein, such as, for example, gel filtration chromatography can be used without any particular limitations.

The solvents available for above-mentioned extraction are those approved by the Japanese Health, Labour and Welfare Ministry to be used for preparing health food products or the like, and therefore this extract may also be used as a material for health food products.

The therapeutic agent for polycystic ovary syndrome (PCOS) under the present invention may further contain a carrier and/or a diluent which are(is) pharmaceutically acceptable in addition to the extract of mushrooms as the active ingredient thereof. As the carrier, cellulose, calcium monohydrogen phosphate, sucrose fatty acid ester, silicon dioxide, methylcellulose, lactose, or the like can be used. As the diluent, water, glycerol, or the like can be used. Also, general additives such as preservatives, stabilizers, excipients, binders, disintegrators, sweeteners, or the like may be further added.

Moreover, the therapeutic agent for polycystic ovary syndrome (PCOS) under the present invention may be administered orally, parenterally, or transdermally. It is generally desirable that the amount of the active ingredient to be administered be properly decided depending on the body weight of the patient, the nature and the state of the disease, the administration route, or the like. In the case of oral administration, the dose per day is preferably 50 to 800 mg/person, more preferably 100 to 500 mg/person, and most preferably 200 to 350 mg/person, and this is administered once or in several divided doses a day.

The extract of mushrooms under the present invention may be used alone or concomitantly with other pharmacologically active substances. Examples of forms suitable for administration include tablets (plain tablets), coated tablets, capsules, suppositories, solutions, syrups, emulsions, dispersive powders, and the like. It is preferable that the tablets or the like contain the extract of mushrooms under the present invention in an amount of 3 to 80% by mass, and more preferably 5 to 50% by mass.

The tablets can be prepared by mixing the extract of mushrooms under the present invention with at least one active ingredients and known excipients including inactive components such as calcium carbonate, calcium phosphate, lactose, or the like; disintegrators such as corn starch, alginic acid, or the like; binders such as starch, gelatin, or the like; lubricants such as magnesium stearate, talc, or the like; and/or agents enabling a delayed release such as carboxymethylcellulose, cellulose acetate phthalate, polyvinyl acetate, or the like, or alternatively the tablets can be prepared by mixing the extract with another pharmacologically active ingredient. The tablets may be composed of several layers.

The coated tablet can be prepared by coating a core prepared in the same manner as that of the tablets with a substance conventionally used for coating tablets, such as, for example, gum arabic, talc, titanium dioxide, methylcellulose, sucrose, or the like. In order to enable delayed release or avoid incompatibility, the core may be composed of several layers and may contain the above-mentioned excipients for the tablets.

Also, syrups containing the extract of mushrooms under the present invention or a mixture of this and other pharmacologically active substances may contain sweeteners such as saccharin, cyclamate, glycerol, sucrose, or the like, and flavor-improvers, such as, for example, flavoring agents such as vanillin, orange extract, or the like. Suspension auxiliary agents or thickeners such as sodium carboxymethylcellulose or the like; humectants such as a condensate of aliphatic alcohol and ethylene oxide, or the like; or preservatives such as p-hydroxybenzoate or the like may also be contained.

Also, the capsules containing the extract of mushrooms under the present invention or a mixture of this and other pharmacologically active ingredients may be prepared by, for example, mixing these ingredients with inactive carriers such as lactose, sorbitol, or the like, and encapsulating the mixture into a gelatin capsule or the like.

Also, suppositories can be prepared by mixing the extract of mushrooms under the present invention or a mixture of the extract and other pharmacologically active ingredients with conventionally-used carriers, specifically a neutral lipid, polyethyleneglycol, a derivative thereof, or the like.

Also, the extract of mushrooms under the present invention or a mixture of this and other pharmacologically active ingredients may be applied to food such as health food, functional food, or general food. Since the glycoprotein is contained in the extract of mushrooms under the present invention, it is very safe and so the above-mentioned food can be taken over an extended period of time. These foods may contain vitamins, minerals, herbs, or other nutritional materials, in addition to the above-mentioned supplemented components.

The following examples do not limit the scope of the present invention and are provided merely for illustrative purposes.

EXAMPLES

Preparation Example 1

Preparation of the Extract of Mushrooms (*Grifola frondosa*)

5 L of 95% aqueous ethanol was added to 1000 g of dried *Grifola frondosa* fruiting body powder, stirred for 2 to 3 hours at room temperature, and then filtered to remove the ethanol-soluble components.

Then, 5 L of deionized water was added to the obtained residue, and then extracted for 2 hours while stirring at 100 to 120° C. This hot-water-extracted liquid was concentrated to half of the original value, followed by adding ethanol until the final ethanol concentration became 50 to 75% by value. This was allowed to stand in a low-temperature chamber at 4 to 10° C. for 8 to 12 hours, and solid substances such as precipitates or floating matter, which were insoluble components, were removed by centrifugation to obtain a supernatant.

From this supernatant, a fraction having a molecular weight of 14,000 Dalton or more was collected by dialysis, and thus an extract of *Grifola frondosa* was obtained.

In order to analyze this extract of *Grifola frondosa*, it was purified by gel filtration chromatography, and thus approximately 21 g of a brown substance was obtained. This purified extract of *Grifola frondosa* was tested positive for the biuret reaction and Fehling's reaction, and thus was confirmed to contain a protein portion and saccharide portion.

Analysis Example

Analysis of Purified Extract of *Grifola frondosa*

With respect to the purified extract of *Grifola frondosa* obtained as described above, quantitative analysis of the simple protein portion thereof was carried out by using the Bradford method. The analysis on the constituent amino acids of the simple protein portion was carried out using an automatic amino-acid analyzer (Hitachi L-8500A Amino Acid Analyzer). Also, the quantitative analysis of the saccharide portion was carried out by using the phenol-sulfuric acid method, and the analysis with respect to the constituent of the saccharide portion was carried out by using high-performance liquid chromatography (HPLC). The measurement of the molecular weight was carried out by using SDS-PAGE electrophoresis. Also, a $^1$H-NMR measurement was carried out.

Results of the analysis with respect to mass ratios of the simple protein portion and the saccharide portion in the purified extract of *Grifola frondosa* are shown in Table 1. The substance was confirmed to be a glycoprotein.

TABLE 1

| Sample | Protein | Saccharide |
|---|---|---|
| 1 | 83.8% | 16.2% |
| 2 | 75.8% | 24.2% |
| 3 | 86.7% | 13.3% |
| 4 | 79.8% | 20.2% |

A chart drawing of results of the analysis by high-performance liquid chromatography (HPLC) on the extract of *Grifola frondosa* obtained in Preparation Example 1 is shown in FIG. 1. In FIG. 1, the peak at 7.189 was identified to be a glycoprotein.

The glycoprotein, which was the main component of the obtained extract of *Grifola frondosa*, had the following characteristics.

Appearance: Brown and hygroscopic powder
Solubility: Soluble in water and alkaline solution
Stability: Stable at high temperature and in ethanol
Chemical constituent: Simple protein portion:Saccharide portion=75:25 to 90:10 (see Table 1)
The constituent amino acids of the protein portion: asparagine, glutamine, serine, threonine, glycine, alanine, valine, cysteine, methionine, isoleucine, leucine, tyrosine, phenylalanine, lysine, histidine, arginine, proline
Components of the saccharide portion: galactose, mannose, glucose, N-acetyl-glucosamine, fucose
$^1$H-NMR spectrum: 3.0473, 3.8983, 6.8500, 7.3150
Average molecular weight: 20,000 Dalton Preparation Example 2

Preparation Method of a Tablet

A tablet having the following components was prepared using the extract of *Grifola frondosa* which was obtained in Preparation Example 1.

| Tablet | Per tablet |
|---|---|
| Active ingredients: | |
| Extract of *Grifola frondosa* (powdered) | 36 mg |
| Dried *Grifola frondosa* powder | 250 mg |
| Excipients: | |
| Fine crystalline cellulose | 264 mg |
| Calcium monohydrogen phosphate | 20 mg |
| Sucrose fatty acid ester | 20 mg |

-continued

| Tablet | Per tablet |
|---|---|
| Fine silica dioxide | 10 mg |
| Coating material: | |
| Methylcellulose | 1 to 1.5% by mass of the tablet |

The dried *Grifola frondosa* powder means a powder obtained by merely drying and pulverizing *Grifola frondosa* without extracting with ethanol. The above-mentioned extract of *Grifola frondosa* (powdered) and the dried *Grifola frondosa* powder were mixed with the finely pulverized excipients and granulated, dried, pulverized, and tableted to make tablets having a proper form and size, followed by coating the tablets with the coating material.

Results of physical analysis and microbial test on the obtained tablet are shown in the following. This tablet was confirmed to satisfy the standards defined in the Pharmaceutical Affairs Law.

| Item of analysis: | |
|---|---|
| Disintegration time | Not more than 45 minutes |
| Weight variation | 600 mg ± 5% |
| Microbial test: | |
| Total plate count | Not more than 3000 |
| Yeast and mold | Not more than 300 |
| *Salmonella* | Absent |
| *Escherichia coli* | Absent |

Preparation Examples 3 to 6

Preparation and Analysis of Extracts from *Lentinus edodes*, *Agaricus blazei Murill*, *Ganoderma lucidum*, and *Pleurotus ostreatus*

Figure 2:
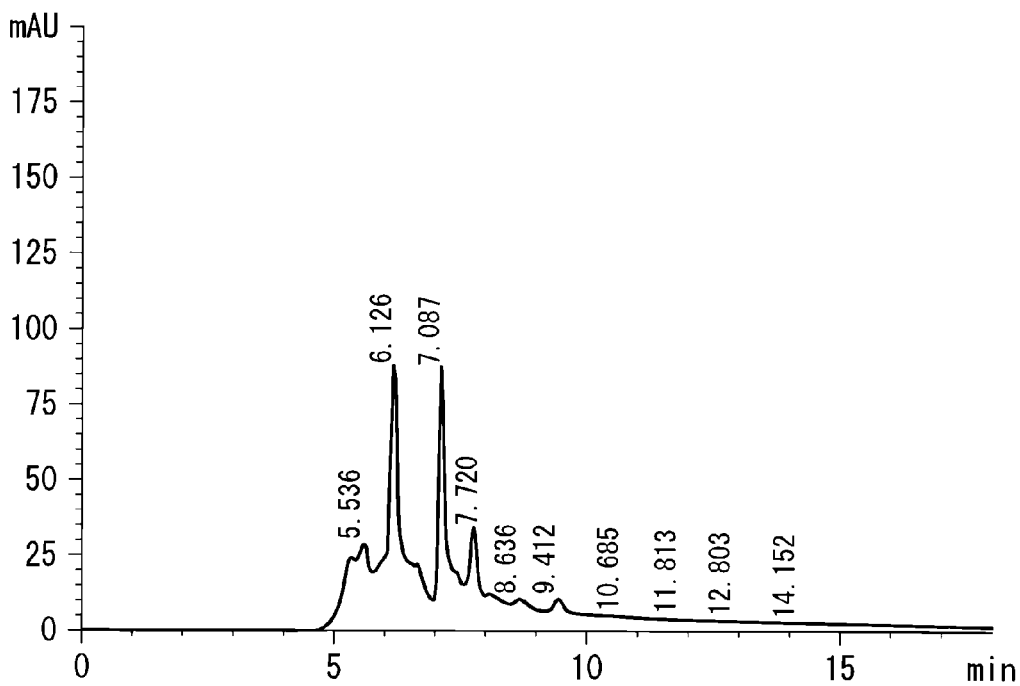
FIG. 2 is a chart drawing indicating a result of an analysis using high-performance liquid chromatography (HPLC) on an extract of *Lentinus edodes* obtained in Preparation Example 3. (Preparation Example 3)
Figure 3:
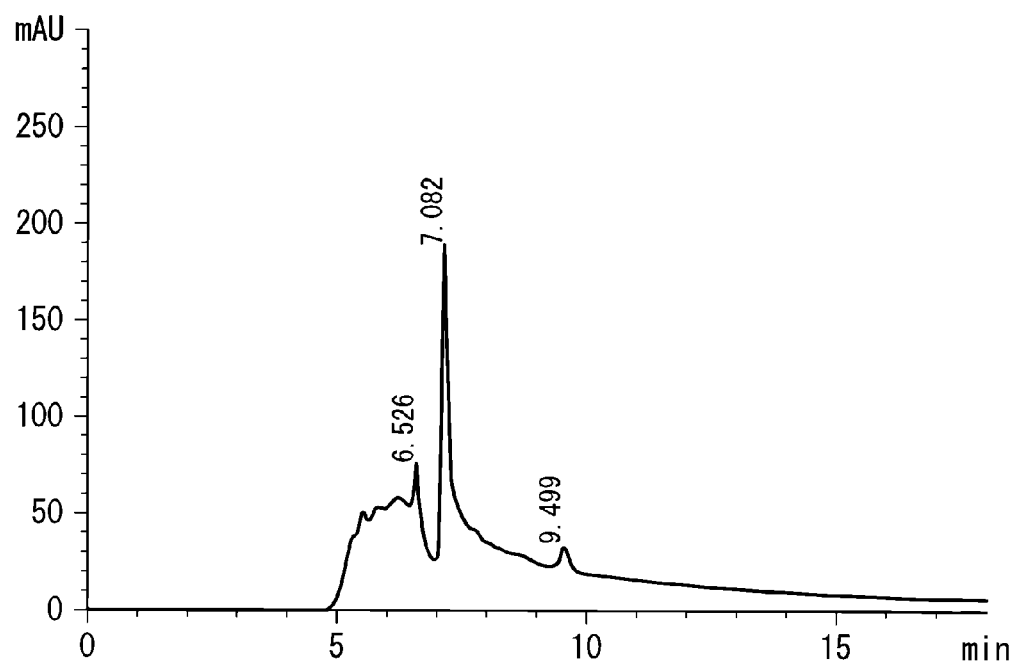
FIG. 3 is a chart drawing indicating a result of an analysis using high-performance liquid chromatography (HPLC) on an extract of *Agaricus blazei Murill* obtained in Preparation Example 4. (Preparation Example 4)
Figure 4:
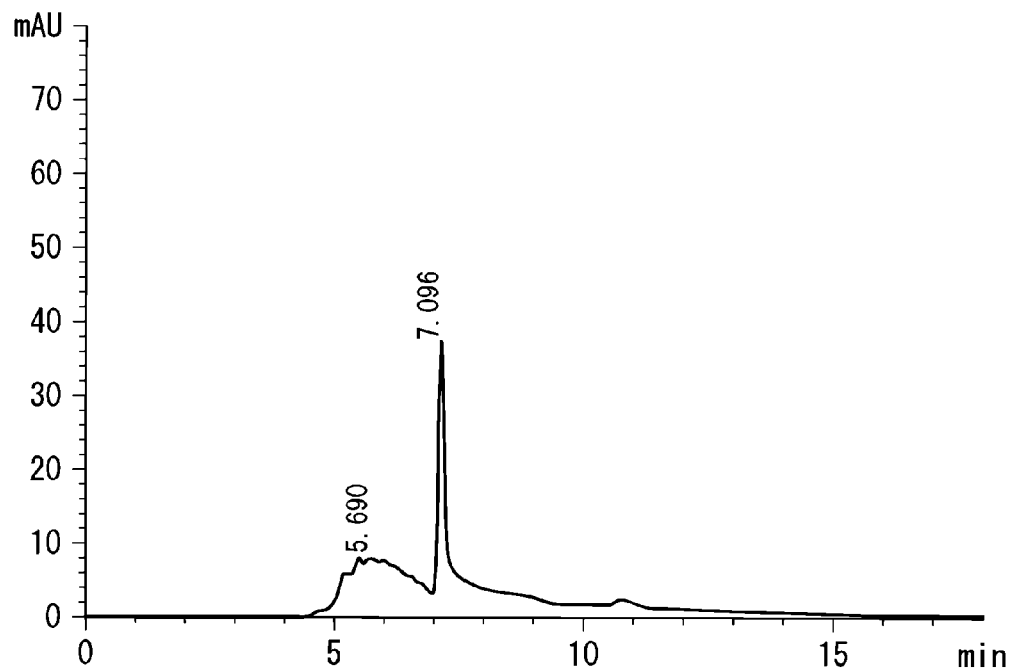
FIG. 4 is a chart drawing indicating a result of an analysis using high-performance liquid chromatography (HPLC) on an extract of *Ganoderma lucidum* obtained in Preparation Example 5. (Preparation Example 5)
Figure 5:
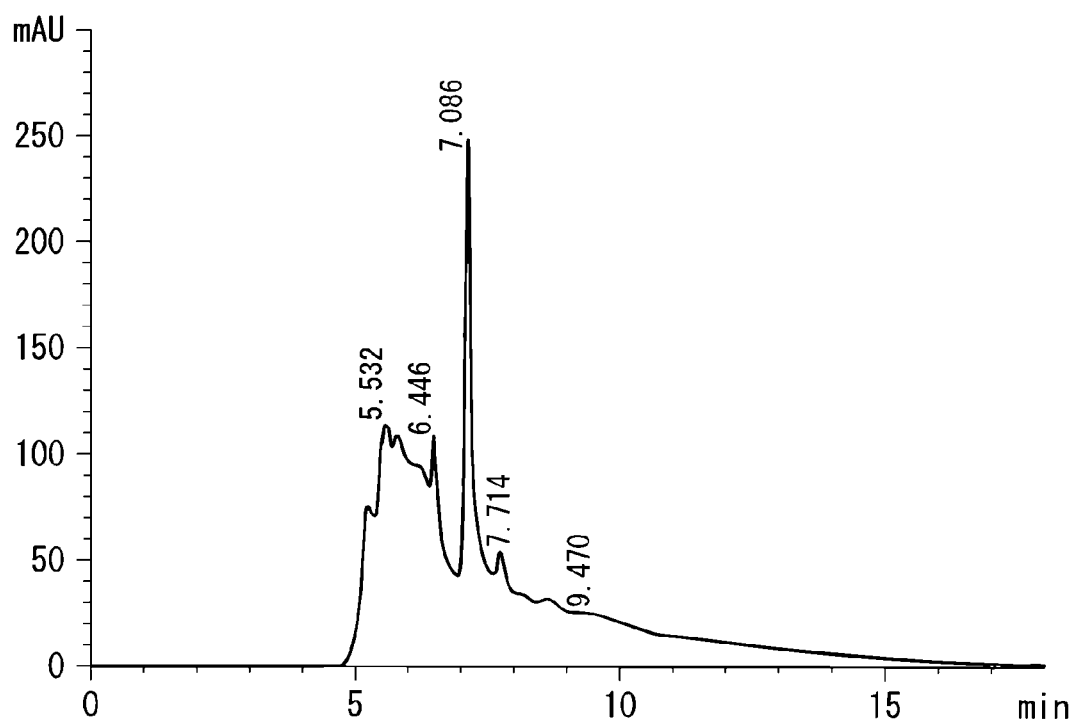
FIG. 5 is a chart drawing indicating a result of an analysis using high-performance liquid chromatography (HPLC) on an extract of *Pleurotus ostreatus* obtained in Preparation Example 6. (Preparation Example 6)

*Lentinus edodes* (Preparation Example 3), *Agaricus blazei Murill* (Preparation Example 4), *Ganoderma lucidum* (Preparation Example 5), and *Pleurotus ostreatus* (Preparation Example 6) were used instead of *Grifola frondosa*, for extraction in the same manner as that in Preparation Example 1. The measurements by HPLC were carried out in the same manner as in the above-mentioned analysis example. FIG. 2 shows a chart drawing of a result of the analysis by HPLC on the extract of *Lentinus edodes* extract, FIG. 3 shows that on *Agaricus blazei Murill*, FIG. 4 that on *Ganoderma lucidum*, and FIG. 5 shows that on *Pleurotus ostreatus*. In FIGS. 2 to 5, each peak was recognized at approximately the same position of 7.189, which is the peak position of the extract of *Grifola frondosa* in Preparation Example 1, that is, 7.087 (FIG. 2), 7.082 (FIG. 3), 7.096 (FIG. 4), or 7.086 (FIG. 5), and thus a component similar to the extract of *Grifola frondosa* in Preparation Example 1 was respectively confirmed to be contained.

Test Example 1

Administration to Patients Suffering from Polycystic Ovary Syndrome (PCOS)

Among outpatients diagnosed with polycystic ovary syndrome (PCOS), 18 patients with anovulation over 3 months or more were randomly divided in two groups. The tablet prepared in Preparation Example 2 described above (tablet made under the present invention) was administered to the test group at a dose of 9 tablets per day in three equally divided doses. To the control group, Shakuyaku-kanzo-to was administered at a dose of 7.5 g per day in three equally divided doses. Each administration was continued over 12 weeks (three cycles) while the patients of each group monitored their basal body temperature to check for the existence of ovulation.

Results of the ovulation rates based on the number of patients showing ovulation are compared as shown in Table 2. Also, results of the number of cycles of ovulation are shown in Table 3.

TABLE 2

| Treatment | Number of patients | Number of patients showing ovulation | Rate of patients showing ovulation |
|---|---|---|---|
| Tablet according to the present invention | 8 | 6 | 75% |
| Shakuyakukanzoto | 10 | 1 | 10% |

TABLE 3

| Treatment | Number of cycles | Number of cycles of ovulation | Rate of cycles of ovulation |
|---|---|---|---|
| Tablet according to the present invention | 24 cycles | 11 cycles | 46% |
| Shakuyakukanzoto | 30 cycles | 3 cycles | 10% |

As shown in Table 2, the comparison of the ovulation rate based on the number of patients who were administered the tablet prepared in Preparation Example 2 described above (tablet made under the present invention) with that of those who were administered Shakuyaku-kanzo-to revealed that the tablet made under the present invention: Shakuyaku-kanzo-to=75%:10%. Also, as shown in Table 3, the comparison based on the number of cycles with ovulation revealed that the tablet made under the present invention: Shakuyaku-kanzo-to=46%:10%. According to Fisher's exact probability test, the p value was less than 0.05, and thus a significant difference was recognized and it was confirmed that the therapeutic agent for polycystic ovary syndrome (PCOS) under the present invention was superior to Shakuyaku-kanzo-to. Also, side effects were not recognized in either group, and thus it was confirmed that the therapeutic agent for polycystic ovary syndrome (PCOS) under the present invention is very safe.

Test Example 2

Safety Test of the Extract of Mushroom

A safety test was carried out using 10 male and 10 female healthy 4-week-old ICR mice. These mice were weighed 4 hours after starvation, and a solution in which the extract of *Grifola frondosa* obtained in Preparation Example 1 was dissolved in distilled water was forcibly administered to respective male and female mice at a single dose of 2,000 mg/kg of body weight using a gastric sonde. To control groups, 0.7 mL of purified water was administered to male mice and 0.6 mL of purified water was administered to female mice in the same manner. The observation period was 14 days and autopsy was carried out on all mice after the end of the observation period.

The male and female mice did not die during the observation period and no abnormality was found with respect to their general conditions and body weight. Under the autopsy, no abnormality was found in the major organs of any of the tested mice. Accordingly, each value of $LD_{50}$ of the extract of mushrooms according to the present invention to be orally administered in a single dose to each male and female mouse was considered to be 2,000 mg/kg of body weight or more, and thus it was confirmed that the extract of mushrooms according to the present invention was very safe.

INDUSTRIAL APPLICABILITY

Since the therapeutic agent for polycystic ovary syndrome (PCOS) under the present invention contains the extract of mushrooms as the active ingredient thereof, the therapeutic agent is safe, exhibits few, if any, side effects, demonstrates excellent effects to induce ovulation, and is safely available for not only females who desire to bear children, but also for unmarried or young females.

The invention claimed is:

1. A method for treating polycystic ovary syndrome, comprising
administering to a person in need thereof an effective amount of a therapeutic agent for treating polycystic ovary syndrome comprising an extract of mushrooms, which are at least one selected from the group consisting of *Grifola frondosa, Polyporus umbellatus, Meripilus giganteus, Grifola albicans, Lentinus edodes, Agaricus blazei Murill, Agaricus bispirus, Ganoderma applanatum, Fomitopsis pinicola, Coriolus versicolor, Ganoderma lucidum, Pleurotus ostreatus, Pleurotus eryngii, Hericium erinaceus, Cordyceps sinensis, Cordyceps sobolifera, Auricularia auricula, Tremella fuciformis,* and *Phellinus linteus.*

2. The method according to claim 1, wherein the mushrooms are at least one selected from the group consisting of *Grifola frondosa, Lentinus edodes, Agaricus blazei Murill, Ganoderma lucidum,* and *Pleurotus ostreatus.*

3. The method according to claim 2, wherein the mushrooms are *Grifola frondosa.*

4. The method according to claim 1, wherein the extract of the mushrooms is prepared by a process comprising:
   (1) treating a raw material of the mushrooms with ethanol having a concentration of 90% or more, and thereby removing ethanol-soluble components to obtain a residue;
   (2) subjecting the residue to hot-water extraction and then filtering to obtain a filtrate, adding ethanol to the filtrate until a final ethanol concentration thereof becomes 50 to 75% by volume, removing insoluble components, and thereby obtaining a supernatant; and
   (3) collecting a fraction having a molecular weight of 14,000 Dalton or more from the supernatant.

5. The method according to claim 1, wherein the therapeutic agent is orally administered at a dose per day of 50 to 800 mg/person.

* * * * *